US006225332B1

(12) United States Patent
Miller et al.

(10) Patent No.: US 6,225,332 B1
(45) Date of Patent: *May 1, 2001

(54) COMPOSITIONS CONTAINING HISTAMINE $H_2$ AGONISTS AND METHODS OF USE IN TREATING ALLERGY AND INFLAMMATION

(75) Inventors: Steven T. Miller; Daniel A. Gamache, both of Arlington; John M. Yanni, Burleson, all of TX (US)

(73) Assignee: Alcon Laboratories, Inc., Fort Worth, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/175,633

(22) Filed: Oct. 20, 1998

Related U.S. Application Data

(60) Provisional application No. 60/062,558, filed on Oct. 21, 1997.

(51) Int. Cl.$^7$ .................................................. A61K 31/415
(52) U.S. Cl. ........................................... 514/400; 514/912
(58) Field of Search ...................... 514/400, 912

(56) References Cited

U.S. PATENT DOCUMENTS

| | | |
|---|---|---|
| 3,993,679 | 11/1976 | Hall et al. . |
| 4,315,024 * | 2/1982 | Abelson ........................... 424/273 R |
| 5,010,095 * | 4/1991 | Sterk et al. .......................... 514/400 |
| 5,360,720 | 11/1994 | Miller et al. . |

OTHER PUBLICATIONS

Church, Is Inhibition of Mast Cell Mediator Release Relevant to the Clinical Activity of Anti–Allergic Drugs?, *Agents and Actions*, vol. 18, 3/4, pp. 288–293 (1986).

Clegg et al., Histamine secretion from human skin slices induced by anti–IgE and artificial secretagogues and the effects of sodium cromoglycate and salbutamol, *Clinical Allergy*, vol. 15, pp. 321–328 (1985).

*Goodman and Gillman's the Pharmacological Basis of Terapeutics*, Eighth Edition, Pergamon Press, New York, pp. 575–588 (1990).

Hennawi, M. El, A comparison between 2% and 4% sodium cromoglycate eye drops in the treatment of vernal keratoconjunctivitis, *Current Eye Research*, vol. 2, No. 11, pp. 765–768 (1982/1983).

Irani et al., Mast cell heterogeneity, *Clinical and Experimental Allergy*, vol. 19, pp. 143–155 (1989).

Leino et al., Clinical Trial Of The Topical Use Of Disodium Cromoglycate In Vernal, Allergic And Chronic Conjunctivitis, *Acta Ophthalmologica*, vol. 58, pp. 121–124 (1980).

Meisler et al., Cromolyn Treatment of Giant Papillary Conjunctivitis, *Archives in Ophthalmology*, vol. 100, pp. 1608–1610 (1982).

Miller et al., Human conjunctival mast cell responses in vitro to various secretagogues, *Ocular Immunology and Inflammation*, vol. 4, issue 1, pp. 39–49 (1996).

Ostler, H. Bruce, Acute Chemotic Reaction to Cromolyni, *Archives in Ophthalmology*, vol. 100, No. 1, pp. 412–413 (1982).

Pearce et al., Effect of Disodium Cromoglycate on Antigen Evoked Histamine Release From Human Skin, *Clinical Experimental Immunology*, vol. 17, pp. 437–440 (1974).

Schwartz et al., Mast Cells, *The Lung: Scientific Foundations*, Raven Press, Ltd., New York, Ch. 3.4.11, pp. 601–616 (1991).

Sharif, et al., Emedastine: A Potent, High Affinity Histamine $H_1$–Receptor–Selective Antagonist for Ocular Use: Receptor Binding and Second Messenger Studies, *Journal of Ocular Pharmacology*, vol. 10, No. 4, pp. 653–664 (1994).

Watt et al., Protective effect of lodoxamide tromethamine on allergen inhalation challenge, *Journal of Allergy and Clinical Immunology*, vol. 66, No. 4, pp. 286–294 (1980).

Kohno et al., "Dimaprit, a Histamine $H_2$–Agonist, Inhibits Anaphylactic Histamine Release from Mast Cells and the Decreased Release Is Restored by Thioperamide ($H_3$–Antagonist), but Not by Cimetidine ($H_2$–Antagonist)," *Japan J. Pharmacol.*, vol. 62, pp. 75–79 (1993).

Kleine–Tebbe et al., "Modulation of IgE–mediated histamine release form human leukocytes by a new class of histamine $H_2$–agonists," *Agents Actions*, vol. 35, pp. 185–191 (1992).

* cited by examiner

Primary Examiner—Zohreh Fay
(74) Attorney, Agent, or Firm—Michael C. Mayo; Patrick M. Ryan

(57) ABSTRACT

Compositions containing histamine $H_2$ agonists and methods of use for treating allergy and inflammation of the eye are disclosed.

5 Claims, 1 Drawing Sheet

COMPOSITIONS CONTAINING HISTAMINE H$_2$ AGONISTS AND METHODS OF USE IN TREATING ALLERGY AND INFLAMMATION

The present application claims priority to U.S. provisional Ser. No. 60/062,558 filed Oct. 21, 1997.

The present invention is directed to compositions containing histamine H$_2$ agonists and methods for their use in treating allergy and inflammation. The H$_2$ agonists of the present invention stabilize human conjunctival mast cells. The compositions are used to prevent allergic responses while also treating existing allergic conditions present in the eye. The invention is also directed to methods of preventing and treating allergic responses with the compositions.

BACKGROUND OF THE INVENTION

The eye, particularly the conjunctiva, has a relatively large number of mast cells. When allergens are present, they can bind to immunoglobulins on the surface of these mast cells and trigger the release of cellular contents, known as degranulation. Upon degranulation, mast cell components, including histamine, are released into the environment outside the mast cell. Through a variety of mechanisms, these components can be responsible for symptoms associated with allergic responses such as itching, redness, lid swelling, vasodilatation and chemosis.

Various therapies have been pursued in order to treat the symptoms of allergies. For example, such therapy has included the use of anti-allergics and histamine H$_1$-receptor antagonists (anti-histamines).

Anti-allergics are compounds which prevent, inhibit or alleviate allergic reactions. Disodium cromoglycate (DSCG) has been used as an anti-allergic to treat allergic conditions such as: vernal, allergic or chronic conjunctivitis (Leino et al., Clinical Trial Of The Topical Use Of Disodium Cromoglycate In Vernal, Allergic And Chronic Conjunctivitis, *Acta Ophthalmoloica*, volume 58, pages 121–124, 1980); vernal keratoconjunctivitis (M. El Hennawi, A comparison between 2% and 4% sodium cromoglycate eye drops in the treatment of vernal keratoconjunctivitis, *Current Eye Research*, volume 2, No. 11, pages 765–768, 1982/1983); and giant papillary conjunctivitis (Meisler et al., Cromolyn Treatment of Giant Papillary Conjunctivitis, *Archives in Ophthalmology*, volume 100, pages 1608–1610, 1982). DSCG has been reported to be irritating to some patients (H. Bruce Ostler, Acute Chemotic Reaction to Cromolyni, *Archives in Ophthalmology*, volume 100, No. 1, pages 412–413, 1982). Cyano phenylene dioxamic compounds disclosed generally in U.S. Pat. No. 3,993,679 issued to Hall et al., are also anti-allergic compounds which have been used in preventing allergic reactions resulting in mast cell degranulation. Although these compounds can be anti-allergic, they can also cause eye irritation and systemic side effects; see for example, Watt et al., Protective effect of lodoxamide tromethamine on allergen inhalation challenge, *Journal of Allergy and Clinical Immunology*, volume 66, No. 4, pages 286–294 (1980).

Anti-histamines are compounds which are administered to antagonize the action of histamine, released from mast cells in response to the presence of allergens. As histamine antagonists, they reduce the redness, itching and swelling caused by the action of histamine on the target tissues in the conjunctiva. They serve to prevent or alleviate many of the symptoms which can result from degranulation of mast cells. However, anti-histamines have also been associated with adverse reactions such as diminished alertness, slowed reaction times and somnolence (*Goodman and Gillman's the Pharmacological Basis of Therapeutics*, Eighth Edition, Pergamon Press, New York, pages 575–588 (1990)).

In order to ascertain compounds with specific mast cell stabilizing efficacy, studies have been conducted with various mast cell lines. However, mast cells are recognized as a heterogeneous cell type. For example, it is now well established that the types of mast cells which exist in rodents are different from those in humans. See, for example, *THE LUNG: Scientific Foundations*, Raven Press, Ltd., New York, Chapter 3.4.11 (1991). Moreover, mast cell populations of various tissues within the same species differ in phenotype, biochemical properties, functional and pharmacological responses and ontogeny. These recognized differences in mast cells, both between and within species, are referred to as mast cell heterogeneity. See, for example, Irani et al., Mast Cell Heterogeneity, *Clinical and Experimental Allergy*, volume 19, pages 143–155 (1989). Because different mast cells exhibit different responses to pharmacological agents, it is not obvious that compounds claimed to be anti-allergic ("mast cell stabilizers") will have clinical utility in specific mast cell populations. The assumption that mast cells are a homogeneous population, and that experiments in rat mast cells would be predictive of those in human cells, is also known to be incorrect (Church, Is Inhibition of Mast Cell Mediator Release Relevant to the Clinical Activity of Anti-Allergic Drugs?, *Agents and Actions*, volume 18, No. 3/4, pages 288–293, (1986)).

Examples exist in the art in which mast cell stabilizing drugs inhibit only select populations of mast cells. Disodium cromoglycate is an anti-allergic drug whose local effects are believed to be due to inhibition of mast cell degranulation (Church, Agents and Actions, at 288). This drug was shown to inhibit rodent mast cell degranulation. In human trials, 100 $\mu$M of the drug inhibited mast cells obtained from bronchoalveolar lavage fluid.

In dispersed human lung mast cell preparations, 1000 $\mu$M of the drug was required to inhibit only 25% to 33% of histamine release. Finally, histamine release from human skin mast cells was not inhibited at all by disodium cromoglycate. Pearce et al., Effect of Disodium Cromoglycate on Antigen Evoked Histamine Release from Human Skin, *Clinical Experimental Immunology*, volume 17, pages 437–440 (1974); and Clegg et al., Histamine Secretion from Human Skin Slices Induced by Anti-IgE and Artificial Secretagogues and the Effects of Sodium Cromoglycate and Salbutamol, *Clinical Allergy*, volume 15, pages 321–328 (1985). These data clearly indicate that one can not predict with certainty that drugs which possess inhibitory effects on one mast cell population will affect all mast cell populations.

A disadvantage to the ophthalmic use of reported anti-allergic drugs which in fact have no stabilizing effect on human conjunctival mast cells is an increased dosage frequency. Because the effectiveness of ophthalmic formulations containing drugs which do not have conjunctival mast cell activity stems primarily from a simple irrigation effect, more frequent doses are typically required than for drugs which do inhibit conjunctival mast cell degranulation. Therefore, topical ophthalmic formulations which contain drugs having conjunctival mast cell activity may only need to be applied once every 12–24 hours instead of once every 2–4 hours.

What is needed are drug compounds proven to prevent the release of mediators of allergic response from the mast cells of the human conjunctiva, the target cells for treating allergic eye diseases. What is also needed are local administration methods for the treatment of allergic eye disease. Furthermore, what is needed are prophylactic therapies in contrast with symptom treating approaches.

SUMMARY OF THE INVENTION

Figure 1:
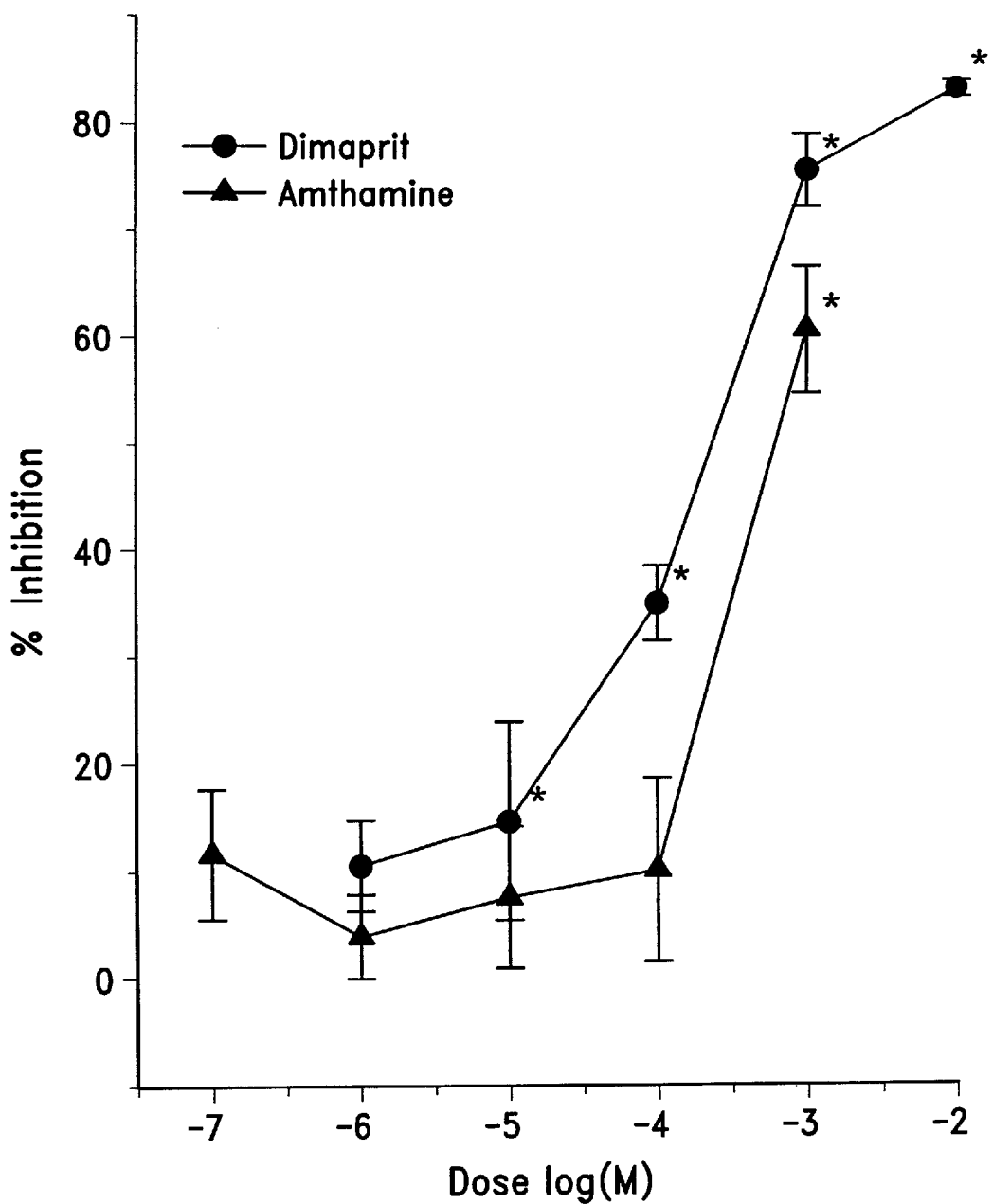
FIG. 1 is a graph illustrating the concentration dependent effect of dimaprit and anithamine on the inhibition of histamine release from human conjunctival mast cells.

The present invention is directed to compositions and methods for the treatment of allergy and/or inflammation of the eye. More specifically, the present invention discloses ophthalmic compositions containing histamine $H_2$ agonists and methods for treating allergy and/or inflammation.

The $H_2$ agonists work by inhibiting the secretion of histamine and/or other pro-inflammatory molecules from human conjunctival mast cells. The decreased secretion of histamine and/or other pro-inflammatory molecules reduces and/or prevents symptoms associated with ocular allergy and inflammation.

DETAILED DESCRIPTION OF THE INVENTION

It has now been discovered that histamine $H_2$ agonists exhibit anti-allergy effects by inhibiting histamine release from human conjunctival mast cells. Additionally, because the $H_2$ agonists inhibit mast cell degranulation, they are believed to be useful as anti-inflammatory agents due to their inhibition of pro-inflammatory mediator release via degranulation. As used herein, the terms "histamine $H_2$ agonists" or "$H_2$ agonists" refer to those molecules which stimulate $H_2$ receptors of the eye, preventing mast cell degranulation.

The compounds of the present invention inhibit human conjunctival mast cell degranulation. While mast cells exist in various tissues and species, there is considerable mast cell heterogeneity within these different sources. Therefore, in order to provide compounds of the present invention which are specific for human conjunctival mast cells, drug compounds need to be tested for inhibition of human conjunctival mast cell degranulation using human conjunctival mast cells. Such efficacy can be determined by using the method described in U.S. Pat. No. 5,360,720 (Miller et al.) and in Miller, et al., "Human conjunctival mast cell responses in vitro to various secretagogues," *Ocular Immunology and Inflammation,* volume 4, issue 1, pages 39–49 (1996) (the "Miller Test"), the entire contents of the forgoing patent and article are incorporated herein by reference.

The present invention contemplates all known and yet to be discovered $H_2$ agonists. Examples of $H_2$ agonists of the present invention include dimaprit, amthamine and impromidine. The most preferred $H_2$ agonist of the present invention is dimaprit.

The histamine $H_2$ agonists of the present invention are available from numerous sources. For example, the $H_2$ agonists may be obtained from Sigma Chemical (St. Louis, Mo.), Research Biochemicals International (Natick, Mass.) and Biomol (Plymouth Meeting, Pa.). As stated above, other $H_2$ agonists may become available through discovery, and these molecules and their methods of discovery and preparation are also contemplated by the present invention. In particular, the $H_2$ agonists of the present invention may be elucidated by various receptor based biological assays. For example, Sharif, et al., Emedastine: A Potent, High Affinity Histamine $H_1$-Receptor-Selective Antagonist for Ocular Use: Receptor Binding and Second Messenger Studies, *Journal of Ocular Pharmacology,* volume 10, no. 4, pages 653–664 (1994) describes a method wherein the affinities of test compounds for the histamine $H_1$, $H_2$ and $H_3$ receptors can be determined.

EXAMPLE 1

The Miller Test is generally performed by the following protocol:

Tissue Preparation

Human conjunctival tissue mast cells are isolated from post-mortem tissue donors obtained within 8 hours of death by various eye banks and transported in Dexsole corneal preservation medium. Tissues are then enzymatically digested by repeated exposure (30 minutes at 37° C.) to collagenase (Type IV) and hyaluronidase (Type I-S) (2 times with 200 U 315 each/gram tissue, then 2–4 times with 2000 U each/gram tissue) in Tyrode's buffer containing 0.1% gelatin. Each digestion mixture is filtered over Nitex® cloth (100 pm mesh) and washed with an equal volume of buffer. Filtrates are centrifuged at 825×g (7 mininutes). Pellets are resuspended in buffer then combined for enrichment over a 1.058 g/L Percoll® cushion. The enriched pellet is then washed and resuspended in supplemented RPMI 1640 medium for equilibration at 37° C.

Equilibration Prior to Treatment or Challenge

The preparations containing the mast cells are then placed in a culture medium, preferably supplemented RPMI 1640, and allowed to equilibrate at about 30°–37° C. for a minimum of about 40 hours.

After equilibrating for a minimum of about 40 hours, the cells may be harvested from the culture (for example, by gentle flushing utilizing pasteur pipettes), pooled and centrifuged.

Cell pellets may then be resuspended in buffer and viability and mast cell number determined by well known methods. The conjunctival mast cells are now prepared for use in mast cell stabilization assays.

Mast Cell Stabilization Assay

All test drugs are placed into solution immediately prior to use. Generally, each compound is dissolved in Tyrode's buffer containing 0.1% gelatin and diluted to an appropriate concentration.

Cells are harvested from the culture plate and counted for viability (trypan blue exclusion) and mast cell number (toluidine blue O). Mast cells (5000/tube; 1 milliliter ("mL," final volume) are then challenged (37° C.) for 15 minutes with goat-anti-human IgE (10 µg/mL) following treatment (1 or 15 minutes; 37° C.) with test drug or Tyrode's buffer. Total and non-specific release controls are exposed to 0.1% Triton X-100 and goat IgG (10 µg/mL), respectively. The reaction was terminated by centrifugation (500×g, 4° C., 10 minutes). Supernatants are stored at −20° C. until analyzed for histamine content by radioimmunoassay ("RIA").

The $IC_{50}$ of each compound (concentration at which 50% of the histamine release was inhibited, as compared to control) was then calculated.

EXAMPLE 2

The $H_2$ agonists, dimaprit and amthamine, were tested in the Miller Test, as described in Example 1, above. Table I and FIG. 1 illustrate the efficacy of dimaprit and amthamine on the inhibition of histamine release from human conjunctival mast cells.

TABLE 1

Effects of dimaprit and amthamine on human conjunctival mast cell release of histamine

| Concentration | % Inhibition of Histamine Release | |
|---|---|---|
| ($\mu$M) | dimaprit | amthamine |
| 0.1 | — | 11.0 6.3 |
| 1.0 | 10.1 ± 4.2 | 3.6 ± 3.9 |
| 10 | 14.4 ± 9.3* | 7.3 ± 6.5 |
| 100 | 35.0 ± 3.5* | 9.9 ± 8.6 |
| 1000 | 75.9 ± 3.5* | 60.5 ± 6.2* |
| 10,000 | 83.6 ± 0.9* | — |

*$p < 0.05$, Dunnett's t-test

The histamine $H_2$ agonists of the present invention are intended for administration to a human patient suffering from ocular allergy and/or inflammation. Preferably, the histamine $H_2$ agonists of the present invention will be administered topically.

The histamine $H_2$ agonists of the present invention may be contained in various types of pharmaceutical compositions, in accordance with formulation techniques known to those skilled in the art. In general, the histamine $H_2$ agonists will be formulated in solutions for topical ophthalmic administration. Solutions, suspensions and other dosage forms are particularly preferred for the treatment of ocular allergy and/or inflammation.

The ophthalmic compositions of the present invention will include one or more histamine $H_2$ agonists in a pharmaceutically acceptable vehicle. Various types of vehicles may be used. Aqueous solutions are generally preferred, based on ease of formulation, biological compatibility, as well as a patient's ability to easily administer such compositions by means of instilling one to two drops of the solutions in the affected eyes. However, the histamine $H_2$ agonists may also be readily incorporated into other types of compositions, such as suspensions, viscous or semi-viscous gels, or other types of solid or semi-solid to compositions. Suspensions may be preferred for histamine $H_2$ agonists which are less soluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Antioxidants may be added to compositions of the present invention to protect the histamine $H_2$ agonists from oxidation during storage. Examples of such antioxidants include vitamin E and analogs thereof, ascorbic acid and butylated hydroxytoluene (BHT).

Ophthalmic products are typically packaged in multidose form. Preservatives are therefore required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquatemium-1, or other agents known to those skilled in the art. Such preservatives are typically employed at a level of from 0.001 to 1.0% weight/volume ("% w/v").

In general, the doses used for the above described purposes will vary, but will be in an effective amount to decrease the secretion of histamine and/or other pro-inflammatory molecules from the eye, and thus eliminate or improve the allergic and/or inflammatory condition of the eye. As used herein, the term "pharmaceutically effective amount" refers to an amount which improves the allergy and/or inflammatory condition of the eye in a human patient. When the compositions are dosed topically, they will generally be in a concentration range of from 0.001 to about 1.0% w/v, with 1–2 drops administered 1–4 times per day.

As used herein, the term "pharmaceutically acceptable carrier" refers to any formulation which is safe, and provides the appropriate delivery for the desired route of to administration of an effective amount of at least one histamine $H_2$ agonists of the present invention.

The compositions of the present invention are further illustrated by the following examples:

EXAMPLE 3

| Ingredient | Amount (wt %) |
|---|---|
| $H_2$ agonist | 0.01–1.0% |
| Phosphate Buffered Saline | 1.0 |
| Polysorbate 80 | 0.5 |
| Purified water | q.s. to 100% |

EXAMPLE 4

| Ingredient | Amount (wt %) |
|---|---|
| $H_2$ agonist | 0.01–1.0% |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor EL | 0.1 |
| Benzalkonium chloride | 0.01 |
| HCl and/or NaOH | pH 7.3–7.4 |
| Purified water | q.s. to 100% |

EXAMPLE 5

| Ingredient | Amount (wt %) |
|---|---|
| $H_2$ agonist | 0.01–1.0% |
| Phosphate Buffered Saline | 1.0 |
| Hydroxypropyl-$\beta$-cyclodextrin | 4.0 |
| Purified water | q.s. to 100% |

The invention in its broader aspects is not limited to the specific details shown and described above. Departures may be made from such details within the scope of the accompanying claims without departing from the principles of the invention and without sacrificing its advantages.

What is claimed is:

1. A method for the treatment of ocular allergy and inflammation comprising topically administering to a human patient a composition comprising a pharmaceutically effective amount of one or more histamine $H_2$ agonist(s) in a pharmaceutically acceptable carrier suitable for topical ocular administration.

2. The method of claim 1, wherein the histamine $H_2$ agonist(s) are selected from the group consisting of dimaprit, amthamine and impromidine.

3. The method of claim 1, wherein the histamine $H_2$ agonist is dimaprit.

4. The method of claim 1, wherein the histamine $H_2$ agonist is amthamine.

5. The method of claim 1, wherein the histamine $H_2$ agonist is impromidine.

* * * * *